(12) United States Patent
Ou et al.

(10) Patent No.: US 11,998,294 B2
(45) Date of Patent: Jun. 4, 2024

(54) SLAVE-END APPARATUS FOR INTERVENTIONAL ROBOT

(71) Applicant: SHENZHEN INSTITUTE OF ADVANCED BIOMEDICAL ROBOT CO., LTD., Shenzhen (CN)

(72) Inventors: Yonghong Ou, Shenzhen (CN); Wenyong Ren, Shenzhen (CN)

(73) Assignee: SHENZHEN INSTITUTE OF ADVANCED BIOMEDICAL ROBOT CO., LTD., Shenzhen (CN)

( * ) Notice: Subject to any disclaimer, the term of this patent is extended or adjusted under 35 U.S.C. 154(b) by 0 days.

(21) Appl. No.: 17/963,173

(22) Filed: Oct. 10, 2022

(65) Prior Publication Data

US 2023/0032469 A1 Feb. 2, 2023

Related U.S. Application Data

(63) Continuation of application No. PCT/CN2022/102921, filed on Jun. 30, 2022.

(30) Foreign Application Priority Data

Jul. 5, 2021 (CN) .......................... 202110759048.0
Jul. 5, 2021 (CN) .......................... 202110759062.0

(Continued)

(51) Int. Cl.
*A61B 34/37* (2016.01)
*B25J 3/00* (2006.01)
(Continued)

(52) U.S. Cl.
CPC ................. *A61B 34/37* (2016.02); *B25J 3/00* (2013.01); *A61B 2034/301* (2016.02); *A61M 25/0113* (2013.01)

(58) Field of Classification Search
CPC .................... A61M 25/0113; A61B 2034/301
See application file for complete search history.

(56) References Cited

U.S. PATENT DOCUMENTS

| 6,096,004 | A | * | 8/2000 | Meglan | .................. | A61B 34/75 |
| | | | | | | 604/95.01 |
| 2008/0045892 | A1 | * | 2/2008 | Ferry | ................. | A61M 25/0113 |
| | | | | | | 604/95.01 |

(Continued)

FOREIGN PATENT DOCUMENTS

| CN | 101999941 A | 4/2011 |
| CN | 107374737 A | 11/2017 |

(Continued)

OTHER PUBLICATIONS

International Search Report issued in corresponding International application No. PCT/CN2022/102248, mailed Aug. 31, 2022.

(Continued)

*Primary Examiner* — Martin T Ton

(57) ABSTRACT

A slave-end apparatus for an interventional robot includes: a body, and a front clamper, a first drive mechanism, a second drive mechanism and a third drive mechanism that are mounted on the body; wherein in a case that the first guide wire runs into the second catheter, the second catheter runs into the first catheter, and the first guide wire, the second catheter and the first catheter are moved along on the body to a desired position, the front clamper and the second drive mechanism take over to clamp the first catheter and the second catheter, the third catheter is caused to run into the second catheter and the second guide wire is caused to run into the third catheter, and the third catheter and the second guide wire are respectively clamped by the second drive mechanism and the third drive mechanism and move on the body.

17 Claims, 3 Drawing Sheets

(30) Foreign Application Priority Data

Aug. 31, 2021 (CN) .......................... 202111009735.7
Aug. 31, 2021 (CN) .......................... 202111009755.4

(51) Int. Cl.
    *A61B 34/30*      (2016.01)
    *A61M 25/01*      (2006.01)

(56) References Cited

U.S. PATENT DOCUMENTS

| | | | |
|---|---|---|---|
| 2009/0105645 A1* | 4/2009 | Kidd | A61M 25/0136 604/108 |
| 2009/0138025 A1 | 5/2009 | Stahler et al. | |
| 2014/0276391 A1 | 9/2014 | Yu | |
| 2014/0277333 A1 | 9/2014 | Lewis et al. | |
| 2016/0338785 A1 | 11/2016 | Kokish et al. | |
| 2017/0151024 A1 | 6/2017 | Deboeuf et al. | |
| 2018/0353250 A1 | 12/2018 | Fournier et al. | |
| 2020/0297973 A1 | 9/2020 | Blacke et al. | |
| 2021/0052339 A1* | 2/2021 | Choi | A61B 34/35 |
| 2022/0313962 A1* | 10/2022 | Kim | A61B 34/35 |
| 2023/0035508 A1* | 2/2023 | Clark | B25J 13/06 |

FOREIGN PATENT DOCUMENTS

| | | |
|---|---|---|
| CN | 107374739 A | 11/2017 |
| CN | 107374740 A | 11/2017 |
| CN | 107744405 A | 3/2018 |
| CN | 107847712 A | 3/2018 |
| CN | 109106449 A | 1/2019 |
| CN | 109171904 A | 1/2019 |
| CN | 109567947 A | 4/2019 |
| CN | 109821138 A | 5/2019 |
| CN | 111529068 A | 8/2020 |
| CN | 112674877 A | 4/2021 |
| CN | 113057718 A | 7/2021 |
| CN | 113693733 A | 11/2021 |
| CN | 113729956 A | 12/2021 |
| EP | 2542290 B1 | 11/2019 |
| JP | 2014113181 A | 6/2014 |
| JP | 2018019987 A | 2/2018 |
| JP | 2020526254 A | 8/2020 |
| JP | 2021052933 A | 4/2021 |
| WO | 2016204437 A1 | 12/2016 |
| WO | 2020061240 A | 3/2020 |
| WO | 2020061240 A1 | 3/2020 |
| WO | 2021011533 A1 | 1/2021 |
| WO | 2021011554 A | 1/2021 |
| WO | 2021011554 A1 | 1/2021 |
| WO | 2022144264 A1 | 7/2022 |
| WO | 2022144266 A1 | 7/2022 |

OTHER PUBLICATIONS

Written Opinion of the International Search Authority in corresponding International application No. PCT/CN2022/102248.
International Search Report issued in corresponding International application No. PCT/CN2022/102921, mailed Sep. 23, 2022.
Written Opinion of the International Search Authority in corresponding International application No. PCT/CN2022/102921.
Decision-to-grant-patent-CN issued in corresponding application No. 202111009735.7, mailed Jul. 13, 2022.

* cited by examiner

SLAVE-END APPARATUS FOR INTERVENTIONAL ROBOT

CROSS REFERENCE TO RELATED APPLICATION

This application is a continuation application of International Application No. PCT/CN2022/102921, filed on Jun. 30, 2022, which claims priorities to: Chinese Patent Application No. 202110759048.0 filed on Jul. 5, 2021, Chinese Patent Application No. 202110759062.0 filed on Jul. 5, 2021, Chinese Patent Application No. 202111009735.7 filed on Aug. 31, 2021, and Chinese Patent Application No. 202111009755.4 filed on Aug. 31, 2021, the disclosures of which are herein incorporated by reference in their entireties.

TECHNICAL FIELD

The present disclosure relates to the technical field of medical robots, applicable to master-slave vascular interventional robots, and in particular, relates to a slave-end apparatus for an interventional robot.

BACKGROUND

Minimally invasive vascular intervention refers to a physician, guided by a digital subtraction angiography (DSA) system, manipulating the movement of a catheter and a guide wire in human blood vessels to treat lesions, so as to achieve the purpose of embolization of abnormal vessels, thrombolysis, dilation of narrow vessels, and the like. At present, interventional therapy has played an important role in the diagnosis and treatment of hundreds of diseases, such as tumor, peripheral vessel disease, great vessel disease, digestive tract disease, nervous system disease, and nonvascular disease. The interventional therapy covers all diseases from the head to the foot of the human body, and has become the first choice for some diseases. Interventional therapy can treat many diseases that cannot be treated in the past or have a poor curative effect without incision of human tissues. In the interventional therapy, the incision (puncture point) only has the size of rice grains. The interventional therapy has the characteristics of no incision, small trauma, rapid recovery and good curative effect, which has been highly valued by domestic and foreign medical circles.

Currently, minimally invasive vascular intervention-assisting robots have developed rapidly due to the involvement of high-end medical equipment and robotic technology. We have also placed investment in research and development.

SUMMARY

A technical problem to be solved by the present disclosure is to provide a slave-end apparatus for an interventional robot which facilitates a physician in interventional procedures.

To solve the above technical problem, the present disclosure provides a slave-end apparatus for an interventional robot. The apparatus includes: a body, a first drive mechanism, a second drive mechanism, a third drive mechanism and a front clamper distal to the first drive mechanism that are successively mounted on the body; wherein the first drive mechanism is configured to clamp and rotate a first catheter and a second catheter, the second drive mechanism is configured to clamp and rotate the second catheter and a third catheter, and the third drive mechanism is configured to clamp and rotate a first guide wire and a second guide wire; and in a case that the first guide wire runs into the second catheter, the second catheter runs into the first catheter, and the first guide wire, the second catheter and the first catheter are respectively clamped by the third drive mechanism, the second drive mechanism and the first drive mechanism and move along a same axial direction on the body toward the front clamper to a desired position, the first catheter, the second catheter and the first guide wire are respectively taken off from the first drive mechanism, the second drive mechanism and the third drive mechanism, the front clamper and the first drive mechanism take over to clamp the first catheter and the second catheter, the third catheter is caused to run into the second catheter and the second guide wire is caused to run into the third catheter, and the third catheter and the second guide wire are respectively clamped by the second drive mechanism and the third drive mechanism and move along the same axial direction on the body toward the front clamper.

Further, the apparatus further includes: a plurality of front clampers; wherein a plurality of first catheters one-by-one pushed by the first drive mechanism to desired positions are respectively clamped by the plurality of front clampers.

Further, the second drive mechanism is configured to clamp and rotate, together with the first drive mechanism, the first catheter and the second catheter.

Further, the second drive mechanism includes: a first assembly configured to clamp and rotate the first catheter and the second catheter, and a second assembly configured to clamp and rotate the second catheter and the third catheter.

Further, the first assembly of the second drive mechanism is configured to clamp an Y adapter connected to the first catheter and the second catheter to clamp the first catheter and the second catheter, and rotate a Luer connector of the Y adapter to drive the first catheter and the second catheter to rotate.

Further, the third drive mechanism is configured to clamp and rotate, together with the second drive mechanism, the second catheter and the third catheter.

Further, the third drive mechanism includes: a first assembly configured to clamp and rotate the second catheter and the third catheter, and a second assembly configured to clamp and rotate the first guide wire and the second guide wire.

Further, the first assembly of the third drive mechanism is configured to clamp an Y adapter connected to the second catheter and the third catheter to clamp the second catheter and the third catheter, and rotate a Luer connector of the Y adapter to drive the second catheter and the third catheter to rotate.

Further, the second assembly is a slave-end guide wire and catheter twisting apparatus for the interventional robot.

Further, the apparatus further includes: a rear clamper; wherein in a case that the third drive mechanism moves to an extreme position and is to be restored to release the second guide wire, the rear clamper is configured to clamp the second guide wire to prevent movement thereof.

Further, the front clamper and the rear clamper are respectively positioned at a front portion and a rear portion of the body; wherein the front clamper and the rear clamper are both mounted on the body and movable relative to the body; or one of the front clamper and the rear clamper is mounted on the body and movable relative to the body, and the other of the front clamper and the rear clamper is mounted separately from the body; or the front clamper and the rear clamper are both mounted separately from the body.

Further, the apparatus further includes: a fourth drive mechanism mounted on the body; wherein the fourth drive mechanism is configured to clamp and rotate, together with the first drive mechanism, the first catheter and the second catheter.

Further, in a case that the first drive mechanism moves to an extreme position and is to be restored to release the first catheter and the second catheter, the fourth drive mechanism is configured to clamp the first catheter and the second catheter to prevent movement thereof.

Further, the fourth drive mechanism is positioned between the first drive mechanism and the second drive mechanism.

Further, the apparatus further includes: a fifth drive mechanism mounted on the body; wherein the fifth drive mechanism is configured to clamp and rotate, together with the second drive mechanism, the second catheter and the third catheter.

Further, in a case that the second drive mechanism moves to an extreme position and is to be restored to release the second catheter and the third catheter, the fifth drive mechanism is configured to clamp the second catheter and the third catheter to prevent movement thereof.

Further, the fifth drive mechanism is positioned between the second drive mechanism and the third drive mechanism.

Further, the fourth drive mechanism and the fifth drive mechanism move along the same axial direction as the first drive mechanism, the second drive mechanism and the third drive mechanism.

Further, the apparatus further includes: an exchange mechanism; wherein the exchange mechanism is a rapid exchange mechanism or a coaxial exchange mechanism.

Further, the exchange mechanism is detachably fixed to the third drive mechanism, or the exchange mechanism and the third drive mechanism are integrally designed.

According to the present disclosure, the physician may remotely manipulate the first drive mechanism, the second drive mechanism and the third drive mechanism to move along the same axial direction on the body, such that a plurality of catheters and a plurality of guide wires collaboratively move to desired positions. In case of replacing the catheter and the guide wire, the front clamper clamps the first catheter to prevent movement thereof. This blocks radiation by X rays and protects health of human bodies. In addition, the robot may more accurately control the catheter and the guide wire, and more complicated operations may be carried out, which not only reduces working intensity, but also avoids severe mistakes.

DETAILED DESCRIPTION

Figure 1:
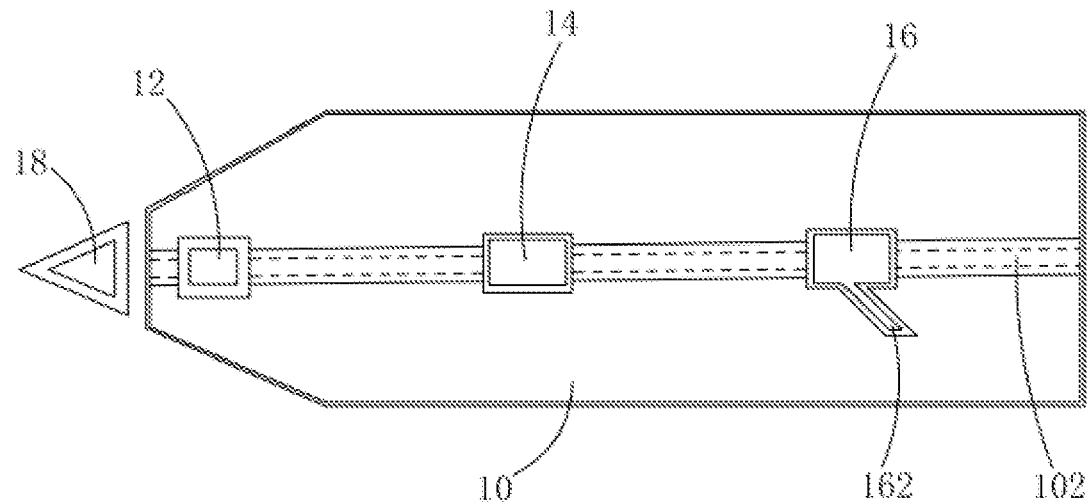
FIG. 1 is a schematic view of a slave-end apparatus for an interventional robot according to a first embodiment of the present disclosure.

For clear description and better understanding of the technical problem to be solved, technical solutions, and advantages of the present disclosure, the present disclosure is further described in detail with reference to the accompanying drawings and specific embodiments. It should be understood that the embodiments described here are only exemplary ones for illustrating the present disclosure, and are not intended to limit the present disclosure.

In the description of the present disclosure, it should be noted that unless otherwise specified and defined, the terms "mounted," "coupled," "connected," "fixed," and derivative forms thereof shall be understood in a broad sense, which, for example, may be understood as fixed connection, detachable connection or integral connection or even connected in a relative movement fashion; may be understood as mechanical connection or electrical connection, or understood as direct connection, indirect connection via an intermediate medium, or communication between the interiors of two elements or interactions between two elements. Persons of ordinary skill in the art may understand the specific meanings of the above terms in the present application according to the actual circumstances and contexts.

In the description of the present disclosure, the terms "length," "diameter," "upper," "lower," "front," "rear," "left," "right," "vertical," "horizontal," "top," "bottom," "inner," "outer," and the like indicate orientations or positional relationships which are based on the illustrations in the accompanying drawings, and these terms are merely for ease and brevity of the description, instead of indicating or implying that the devices or elements shall have a particular orientation and shall be structured and operated based on the particular orientation. Accordingly, these terms shall not be construed as limiting the present disclosure.

The term "distal from" indicates a direction facing towards a patient, and the term "proximal to" indicates a direction facing away from the patient. The terms "up" and "upper" indicate a direction facing away from a direction of gravity, and the terms "bottom," "down," and "lower" indicate a direction facing towards the direction of gravity. The term "forward" indicates a direction along which a guide wire or a catheter moves to the body of the patient. The term "backward" indicates a direction along which the guide wire or the catheter moves out of the body of the patient. The term "inwardly" indicates an inner portion of a feature. The term "outwardly" indicates an outer portion of a feature. The term "rotation" includes "forward rotation" and "reverse rotation," wherein the "forward rotation" indicates a direction along which the guide wire or the catheter rotates to move into the body of the patient, and the "reverse rotation" indicates a direction along which the guide wire or the catheter rotates to move out of the body of the patient.

In addition, terms of "first" and "second" are only used for description, but shall not be understood as indication or implication of relative importance or implicit indication of the number of the specific technical features. Therefore, the features defined by the terms "first" and "second" may explicitly or implicitly include one or more of these features. In addition, in the description of the present disclosure, the term "multiple," "more," or "a plurality of" refers to at least two unless otherwise specified.

It should be noted that, in the absence of conflict, embodiments of the present disclosure and features in the embodiments may be incorporated, which all fall within the protection scope of the present disclosure. In addition, all or part of the steps of the method may be performed in a computer system including a group of computer-executable instructions. Further, although the steps are listed in a sequence of 1, 2, 3 . . . , in some cases, the steps may also be performed in a sequence that is different form the sequence listed herein.

The guide wire herein includes, but is not limited to, a guide wire, a micro guide wire, a stent and the like guiding and supporting interventional medical instruments. The catheter includes, but is not limited to, a guide catheter, a micro catheter, an angiographic catheter, a multifunctional catheter (also referred to as a middle catheter), a thrombolytic catheter, a balloon dilatation catheter, a balloon-expandable stent catheter and the like interventional medical instruments for treatment.

Figure 2:
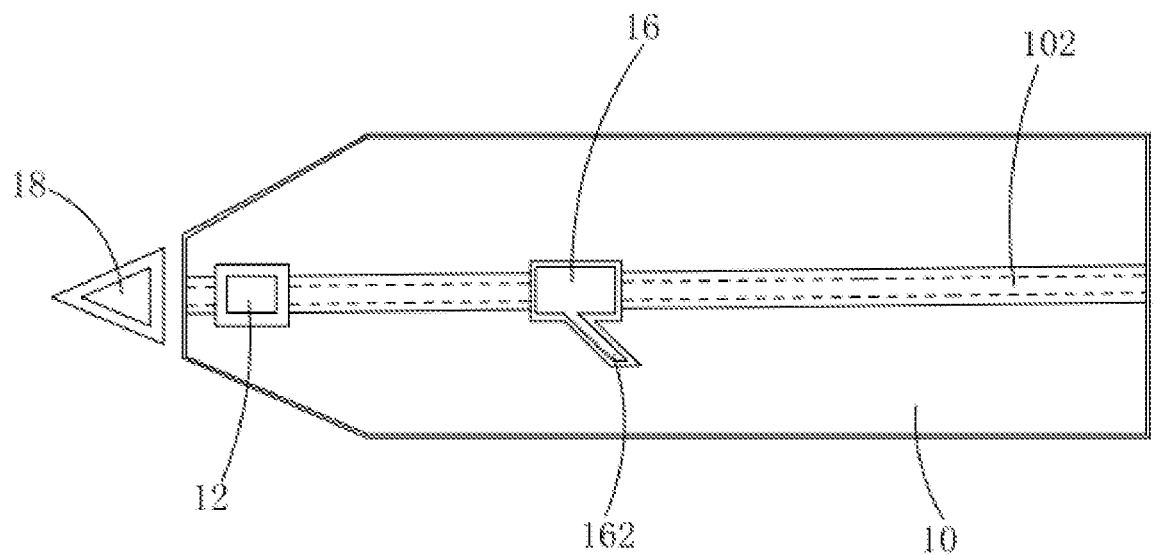
FIG. 2 is another schematic view of the slave-end apparatus in FIG. 1.

As illustrated in FIG. 1 and FIG. 2, a first embodiment of the present disclosure provides a slave-end apparatus for an interventional robot. The apparatus includes: a body 10, drive mechanisms 12, 14 and 16 that are movably mounted on the body 10, a front clamper 18 and a rear clamper (not illustrated).

The body 10 is elongated, and is provided with a linear guide rail 102. The drive mechanisms 12, 14 and 16 are successively fixed on the guide rail 102, and are slidable along the guide rail 102.

Each of the drive mechanisms is configured to clamp, push (including forward movement and backward movement) and rotate (including forward rotation and reverse rotation) the catheter and the guide wire, or may be configured to simultaneously clamp, push (including forward movement and backward movement) and rotate (including forward rotation and reverse rotation) both the catheter and the guide wire, such that a plurality of catheters and a plurality of guide wires collaboratively move. The specific structures of the drive mechanisms 12, 14 and 16 are not necessarily identical, but may be different from each other, as long as the catheter and the guide wire can be clamped, pushed and/or rotated. In this embodiment, the specific structures of the drive mechanisms 14 and 16 are identical, and the drive mechanism 12 has a different structure. The drive mechanism 14 includes: a first assembly configured to cooperate with the drive mechanism 12 to clamp and rotate one catheter, and a second assembly configured to cooperate with the drive mechanism 12 to clamp and rotate another catheter. The drive mechanism 16 includes: a first assembly configured to cooperate with the second assembly of the drive mechanism 14 to clamp and rotate the another catheter, and a second assembly configured to cooperate with the second assembly of the drive mechanism 14 to clamp and rotate the guide wire. The drive mechanism 16 includes a rapid exchange mechanism 162 configured to cooperate with the first assembly of the drive mechanism 16.

In this embodiment, the drive mechanism 12, and the second assemblies of the drive mechanisms 14 and 16 may be the slave-end guide wire and catheter twisting apparatus for the interventional robot as disclosed in Chinese Patent Application No. 202110674959.3, the disclosure of which is incorporated herein in its entirety.

The front clamper 18 is positioned at a front portion of the body 10, distal to the drive mechanisms 12 and 14. The rear clamper is positioned at a rear portion of the body 10. For details, reference may be made to the description of the rear clamper 70. In this embodiment, the front clamper 18 and the rear clamper are fixed on the body 10, and may be movable relative to the body 10 where necessary. In other embodiments, the front clamper 18 and the rear clamper may also be mounted separately from the body 10.

Before an operation, some preparations need to be made. Specifically, a first catheter, a second catheter and a first guide wire that are suitable (for example, those with suitable lengths and diameters) are selected, and the first catheter and the second catheter are washed with normal saline and exhausted. The second catheter is led into the first catheter to go beyond the first catheter by a distance, and the first guide wire is led into the second catheter to go beyond the second catheter by a distance. For example, the head of the first guide wire goes beyond the second catheter by about 10 cm, this process is completed in the catheter. The drive mechanisms 12, 14 and 16 are disposed at proper positions, the first catheter, the second catheter and the first guide wire are together placed and led into an introducer (for example, femoral artery, radial artery or the like) of a patient for operation, the first assemblies of the drive mechanisms 12 and 14 are caused to cooperate to clamp the first catheter, the second assembly of the drive mechanism 14 and the first assembly of the drive mechanism 16 are caused to cooperate to clamp the second catheter, and the second assembly of the drive mechanism 16 is cause to clamp the first guide wire. In this way, the first catheter, the second catheter and the first guide wire are fixed.

When starting the operation, at the operation table, a master-end console (for example, the master-end operation handle for the interventional robot as disclosed in Chinese Patent Application No. 202110654379.8 and the master-end control module as disclosed in Chinese Patent Application No. 202110649908.5, the disclosures of which are incorporated herein in their entireties) is employed to remotely manipulate the drive mechanisms 12, 14 and 16 to move. The master-end console is spatially isolated from a catheter room, and the master-end console and the catheter room are deployed in different regions. Specifically, the drive mechanisms 12, 14 and 16 cooperate to clamp the first catheter, the second catheter and the first guide wire and move along the guide rail 102 to drive the first catheter, the second catheter and the first guide wire to move forward, and the drive mechanisms 12, 14 and 16 simultaneously or non-simultaneously rotate the first catheter, the second catheter and the first guide wire, such that the first catheter, the second catheter and the first guide wire are collaboratively pushed forward. In this process, it needs to be constantly ensured that the second catheter goes beyond the first catheter by a distance, and the first guide wire goes beyond the second catheter by a distance. In a case that the first catheter, the second catheter and the first guide wire reach some positions of the vessel, the drive mechanisms 12, 14 and 16 need to be remotely manipulated by the master-end console, to drive the first catheter, the second catheter and the first guide wire to move forward and backward, and rotate forward and rotate reversely for multiple times for fine adjustment.

In this embodiment, the first assemblies of the drive mechanisms 14 and 16 respectively clamp, via the Y adapter, the first catheter and the second catheter. That is, the first catheter and the second catheter are both connected to the Y adapter; the Y adapter is fixed on the drive mechanisms 14 and 16; the first assemblies of the drive mechanisms 14 and 16 clamp the Y adapter and rotate a Luer connector of the Y adapter; and under cooperation of the second assemblies of drive mechanisms 12 and 14, the first catheter and the second catheter are rotated.

In a case that the first catheter moves forward to a desired position, the first catheter is taken off from the first assemblies of the drive mechanisms 12 and 14; and the front clamper 18 clamps the first catheter to prevent movement thereof. The second catheter is taken off from the second assembly of the drive mechanism 14 and the first assembly of the drive mechanism 16, and the drive mechanisms 12 and 14 are caused to move backward along the guide rail 102 to clamp the second catheter. The drive mechanism 16 may be remotely manipulated by the master-end console to drive the first guide wire to move backward, or the first guide wire may be moved backward. In a case that the first guide wire moves backward to the introducer, the first guide wire is taken off from the second assembly of the drive mechanism 16, and is soaked into heparin water. It should be noted that in this process, the first catheter shall not be pushed, to prevent the head of the first catheter from moving in the vessel.

The drive mechanism 16 is caused to move backward to a suitable position. A third catheter (for example, a micro catheter) and a second guide wire that are thinner (for example, with a diameter of 0.014 in) are selected. The second guide wire is led into the third catheter, which are then led into the second catheter, and the third catheter and the second guide wire are respectively clamped by the second assembly of the drive mechanism 14, the first assembly of the drive mechanism 16 and the second assembly of the drive mechanism 16. In this way, the third catheter and the second guide wire are fixed. In this embodiment, the third catheter is connected to the Y adapter; the Y adapter is fixed on the drive mechanism 16, and is clamped by the first assembly of the drive mechanism 16; and a Luer connector of the Y adapter is rotated, under cooperation of the second assembly of the drive mechanism 14, to drive the third catheter to rotate. With respect to the front clamper 18 configured to clamp the first catheter, the front clamper 18 may also rotate the first catheter by rotating the Luer connector of the Y adapter.

Further, the drive mechanisms 12, 14 and 60 are further remotely manipulated to move by using the master-end console. For details about the specific process, reference may be made to the forward movement of the first catheter, the second catheter and the first guide wire, which are thus not described herein any further. The second catheter is caused to advance to farther vessel sites, to facilitate pushing of the third catheter and the second guide wire to the lesion of the patient for operation (the narrow vessel site) that is farther. In this process, the first catheter needs to be driven to rotate by the front clamper 18. The position of the second guide wire is determined by contrast radiography. In a case that the second guide wire reaches a designated position (generally, the second guide wire needs to run through the lesion of the patient for operation, except possible treatment of aneurysm embolization), the front clamper 18 and the drive mechanisms 12, 14 and 16 respectively fix the first catheter, the second catheter, the third catheter and the second guide wire. In a case that the second guide wire fails to reach the designated position, the drive mechanisms 12, 14 and 16 are repeatedly remotely manipulated to move, until the second guide wire reaches the designated position.

In the case that the second guide wire reaches the designated position, by using the master-end console, the drive mechanism 16 is remotely manipulated to cause the third catheter to move backward. In the meantime, the second guide wire is maintained as not moving. For example, the rear clamper takes over to clamp the second guide wire to prevent movement thereof. In a case that the head of the third catheter moves backward to the introducer, in the catheter room, the third catheter is taken off from the drive mechanisms 14 and 16, and is soaked into the heparin water. In this case, the drive mechanism 16 may take over to clamp the second guide wire, and maintain the front clamper, the drive mechanisms 12 and 14 and the drive mechanism 16 as respectively fixing the first catheter, the second catheter and the second guide wire.

In other embodiments, in a case that the front clamper 18 clamps the first catheter to prevent movement thereof, the drive mechanisms 12, 14 and 16 may be remotely manipulated, by using the master-end console, to drive the second catheter and the first guide wire to move backward together. In a case that the heads of the second catheter and the first guide wire move backward to the introducer, in the catheter room, the second catheter and the first guide wire are taken off from the drive mechanisms 14 and 16, and are soaked into the heparin water. Two catheters and one guide wire that are suitable are selected, and the catheters and the guide wire are placed into the first catheter all together. The drive mechanisms 12, 14 and 16 are caused to be at suitable positions, and the drive mechanisms 12, 14 and 16 are caused to cooperate to clamp the two catheters and the one guide wire. In this way, the two catheters and the one guide wire are fixed. For details about the subsequent process of forward movement, reference may be made to the forward movement of the first catheter, the second catheter and the first guide wire, which are thus not described herein any further.

In other embodiments, the front portion of the body 10 is provided with a plurality of front clampers 18, and in this case, the first catheter may be pushed for multiple times. In a case that the catheter is pushed to a desired position, one of the front clampers 18 is caused to clamp the catheter.

In the catheter room again, the tail of the second guide wire is caused to run into a rapid exchange balloon dilatation catheter. The rapid exchange balloon dilatation catheter moves forward along with the second guide wire. In this case, the rapid exchange mechanism 162 clamps the rapid exchange balloon dilatation catheter.

Further, by using the master-end console, the rapid exchange mechanism 162 is remotely manipulated, such that the rapid exchange balloon dilatation catheter moves forward to the lesion of the patient for operation (not going beyond the head of the second guide wire). In this process, the position and angle of the second guide wire need to be finely adjusted by forward rotation, reverse rotation, forward movement, and backward movement according to actual needs. In a case that the rapid exchange balloon dilatation catheter reaches the lesion of the patient for operation, a contrast medium is filled into the rapid exchange balloon dilatation catheter in the catheter room for pre-dilatation, and a vasodilation effect is determined by contrast radiography. In a case that the vasodilation effect is achieved, the contrast medium is extracted from the rapid exchange balloon dilatation catheter. Further, by using the master-end console, the rapid exchange mechanism 162 is remotely manipulated to move backward to the introducer. In the process that the rapid exchange balloon dilatation catheter moves backwards, the position of the second guide wire remains unchanged. With respect to some operations, vasodilation needs to be performed for multiple times. Therefore, the rapid exchange balloon dilatation catheter may move forward and move backward for multiple times.

Further, in the catheter room again, the rapid exchange balloon dilatation catheter is taken off from the rapid exchange mechanism 162, and then a balloon-expandable stent catheter is caused to run into the second guide wire and to be clamped on the rapid exchange mechanism 162. For details about the specific process, reference may be made to the above process of the rapid exchange balloon dilatation catheter, which are thus not described herein any further.

Further, by using the master-end console, the rapid exchange mechanism 162 is remotely manipulated, such that the rapid exchange balloon dilatation catheter is pushed along the second guide wire to the lesion of the patient for operation (a narrow vessel site that has been expanded). In this process, the position and angle of the second guide wire need to be finely adjusted by forward rotation, reverse rotation, forward movement, and backward movement according to actual needs. When the rapid exchange balloon-expandable stent catheter reaches the lesion of the patient for operation (the vessel side that has been expanded), the position of the rapid exchange balloon-expandable stent catheter is fine-tuned, after determination, the rapid exchange balloon-expandable stent catheter is filled with the contrast medium in the catheter room, such that the stent is shaped. It is confirmed by contrast radiography that the placement of the balloon-expandable stent is correct, i.e., the contrast medium may be extracted and the rapid exchange mechanism 162 is manipulated to drive the rapid exchange balloon-expandable stent catheter to move backward to the introducer, whereas the balloon-expandable stent remains in the lesion of the patient for operation. In the catheter room, the rapid exchange balloon-expandable stent catheter is taken off from the rapid exchange mechanism 162, and is put into the heparin water.

Further, by using the master-end console, the drive mechanisms 12, 14 and 16 are remotely manipulated to move, such that the second catheter and the second guide wire move backward to the introducer. Finally, in the catheter room, the first catheter is pulled out to the introducer, and the first catheter, the second catheter and the second guide wire are taken off from the front clamper 18 and the drive mechanisms 12, 14 and 16, soaks the same into the heparin water, and then the introducer is removed and post-operation treatment is carried out to complete the operation.

In the above process, the rapid exchange catheter is used, and therefore, the catheter needs to be clamped, pushed and rotated by a rapid exchange mechanism 162. In a case that a coaxial exchange catheter is used, where the tail of the second guide wire is caused to run into the coaxial exchange catheter, the coaxial exchange catheter is clamped, pushed and rotated by the coaxial exchange mechanism, such that the coaxial exchange catheter moves forward to an appropriate position along the second guide wire or moves backward to the introducer. Regardless of the rapid exchange mechanism 162 or the coaxial exchange mechanism, the clamping, pushing and rotating of the rapid exchange catheter and the coaxial exchange catheter may be practiced by means of roller driving.

For details about how the master-end console remotely manipulates the drive mechanisms 12, 14 and 16 and the rapid exchange mechanism 162 to move, reference may be made to the master-end control module for the interventional robot as disclosed in Chinese Patent Application 202110649908.5. The control module includes two operation levers, wherein one operation lever is configured to manipulate the drive mechanisms 12 and 14 and the rapid exchange mechanism 162, and this operation lever may manipulate the drive mechanisms 12 and 14 and the rapid exchange mechanism 162 in a time-division manner, and the other operation lever is configured to manipulate the drive mechanism 16. Optionally, the master-end console includes more than two operation levers, for example, four operation levers, which are respectively configured to remotely manipulate the drive mechanisms 12, 14 and 16 and the rapid exchange mechanism 162.

In the above, the movement and control process of the present disclosure has been described by taking "balloon-expandable stent angioplasty" as an example. Indeed, the present disclosure may also be used in a variety of procedures including contrast radiography, embolization, thrombectomy, and the like. The drive mechanisms 12, 14 and 16 and the front clamper 18 may be freely adapted according to the actual needs of the operation, i.e., the drive mechanisms 12, 14 and 16 and the front clamper 18 may all be easily disassembled and assembled. Where more complicated operations are performed, more drive mechanisms and front clampers may be deployed. In a case that more drive mechanisms and front clampers are deployed, the collaborative movement of a plurality of catheters corresponding to one guide wire or corresponding to a plurality of guide wires may be practiced. A rapid exchange mechanism is provided for each drive mechanism that constantly clamps the catheter, and is either removably mounted to the drive mechanism or integrally formed with the drive mechanism. In case of performing simple examination procedures, only two of the drive mechanisms, such as the drive mechanisms 12 and 16 (or the drive mechanisms 12 and 14, wherein a rapid exchange mechanism may be disposed on the drive mechanism 14 according to the actual needs) and the front clamper 162 are used. In the case, the other drive mechanisms are removed from the body 10.

The following describes a control process where in the present disclosure, only the drive mechanisms 12 and 16 and the front clamper 162 collaboratively push two catheters and one guide wire.

In the preparations for the operation, two catheters (a thick catheter and a thin catheter) and two guide wires (a thick guide wire and a thin guide wire) with appropriate diameters and lengths are selected according to the position of a vascular lesion, and the two catheters are washed with normal saline and exhausted. An interventional robot is started to complete initialization. An introducer is placed for a patient for operation. The thick guide wire is led into the thick catheter and is caused to move out of the thick catheter by a distance, and then the thick guide wire and the thick catheter are together placed into the introducer. The first assemblies of the drive mechanism 12 and the drive mechanism 16 are caused to cooperate to clamp the thick catheter (connected to the Y adapter), and the second assembly of the drive mechanism 16 is caused to clamp the thick guide wire. In this way, the thick catheter and the thick guide wire are fixed.

When starting the operation, by using the master-end console, the drive mechanisms 12 and 16 are remotely manipulated to move. The thick catheter and the thick guide wire are respectively caused to collaboratively move forward to the narrow vessel site. For details about the process, reference may be made to the above-mentioned "balloon stent angioplasty." The heads of the thick catheter and the thick guide wire are maintained within an image field of view. In this case, the thick catheter is taken off from the first assemblies of the drive mechanisms 12 and 16; and the front clamper 18 clamps the thick catheter to prevent movement thereof. It should be noted that in this process, the thick catheter shall not be pushed, to prevent the head of the thick catheter from moving in the vessel. The drive mechanism 16 may be remotely manipulated by the master-end console to drive the thick guide wire to move backward, or the thick guide wire may be moved backward. In a case that the thick guide wire moves backward to the introducer, the thick guide wire is taken off from the second assembly of the drive mechanism 16, and is soaked into the heparin water.

The drive mechanisms 12 and 16 are caused to move backward to a suitable position. The thin guide wire is led into the thin catheter, which are then led into the thick catheter, and the thin catheter and the thin guide wire are collaboratively clamped by the drive mechanisms 12 and 16. In this way, the thin catheter and the thin guide wire are fixed. In this embodiment, the thin catheter is connected to the Y adapter; the Y adapter is fixed on the drive mechanism 16, and is clamped by the first assembly of the drive mechanism 16; and under cooperation of the drive mechanism 14, a Luer connector of the Y adapter is rotated to drive the thin catheter to rotate.

Further, by using the master-end console, the drive mechanisms 12 and 16 are remotely manipulated to move. For details about the specific process, reference may be made to the forward movement of the thick catheter and the thick guide wire, which are thus not described herein any further. The thin catheter and the thin guide wire are pushed to the lesion of the patient for operation (the target narrow vessel site) that is farther. The positions of the thin catheter and the thin guide wire are determined by contrast radiography. In a case that the thin catheter and the thin guide wire reach their designated positions (generally, the thin guide wire needs to run through the lesion of the patient for operation, except possible treatment of aneurysm embolization), the drive mechanisms 12 and 16 respectively fix the thin catheter and the thin guide wire.

Further, in the catheter room again, the tail of the thin guide wire is caused to run into a rapid exchange balloon-expandable stent catheter. The rapid exchange balloon-expandable stent catheter moves forward along with the thin guide wire and runs into the thin catheter, specifically, the Y adapter connecting the thin catheter. In this case, the rapid exchange mechanism 162 clamps the rapid exchange balloon-expandable stent catheter.

Further, by using the master-end console, the rapid exchange mechanism 162 is remotely manipulated, such that the rapid exchange balloon dilatation catheter moves forward to the lesion of the patient for operation (not going beyond the head of the thin guide wire). In this process, the position and angle of the thin catheter and the thin guide wire need to be finely adjusted by forward rotation, reverse rotation, forward movement, and backward movement according to actual needs. When the rapid exchange balloon-expandable stent catheter reaches the lesion of the patient for operation, the position of the rapid exchange balloon-expandable stent catheter is fine-tuned, after determination, the rapid exchange balloon-expandable stent catheter is filled with the contrast medium in the catheter room, such that the stent is shaped. It is confirmed by contrast radiography that the placement of the balloon-expandable stent is correct, i.e., the contrast medium may be extracted and the rapid exchange mechanism 162 is manipulated to drive the rapid exchange balloon-expandable stent catheter to move backward to the introducer, whereas the balloon-expandable stent remains in the lesion of the patient for operation. In the process that the rapid exchange balloon-expandable stent catheter moves backwards, the positions of the thick catheter, the thin catheter and the thin guide wire remain unchanged. In the catheter room, the rapid exchange balloon-expandable stent catheter is taken off from the rapid exchange mechanism 162, and is put into the heparin water.

Further, by using the master-end console, the drive mechanisms 12 and 16 are remotely manipulated to move, such that the thin catheter and the thin guide wire move backward to the introducer. Finally, in the catheter room, the thick catheter is pulled out to the introducer, the thick catheter, the thin catheter and the thin guide wire are taken off from the front clamper 18 and the drive mechanisms 12 and 16, and are soaked into the heparin water, and then the introducer is removed and post-operation treatment is carried out to complete the operation.

In the above process, in a case that a coaxial exchange catheter is used, where the tail of the thin guide wire is caused to run into the coaxial exchange catheter, the coaxial exchange catheter is clamped, pushed and rotated by the coaxial exchange mechanism, such that the coaxial exchange catheter moves forward to an appropriate position along the thin guide wire or moves backward to the introducer.

Figure 3:
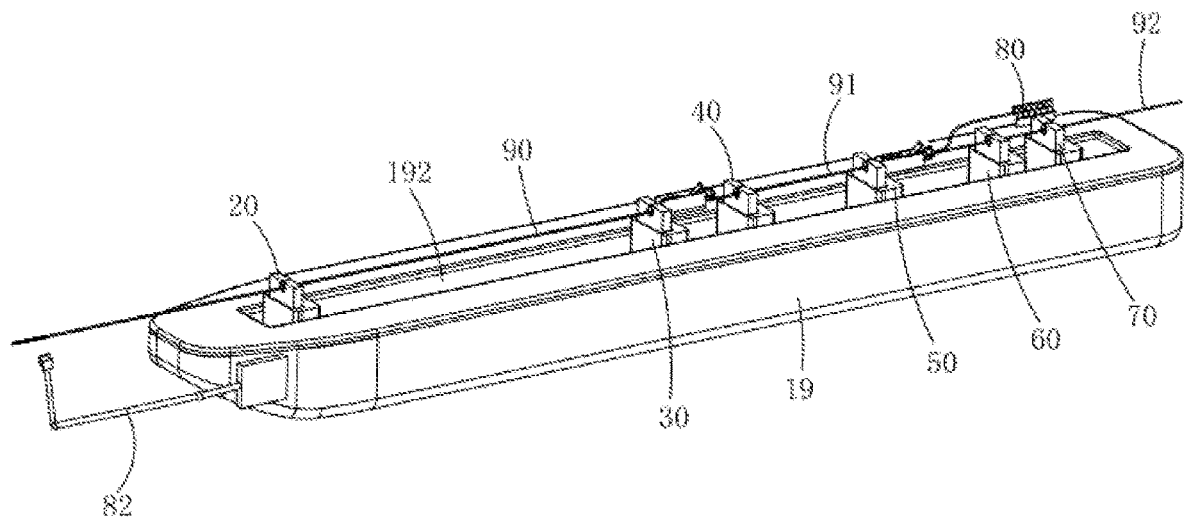
FIG. 3 is a schematic view of a slave-end apparatus for an interventional robot according to a second embodiment of the present disclosure.
Figure 4:
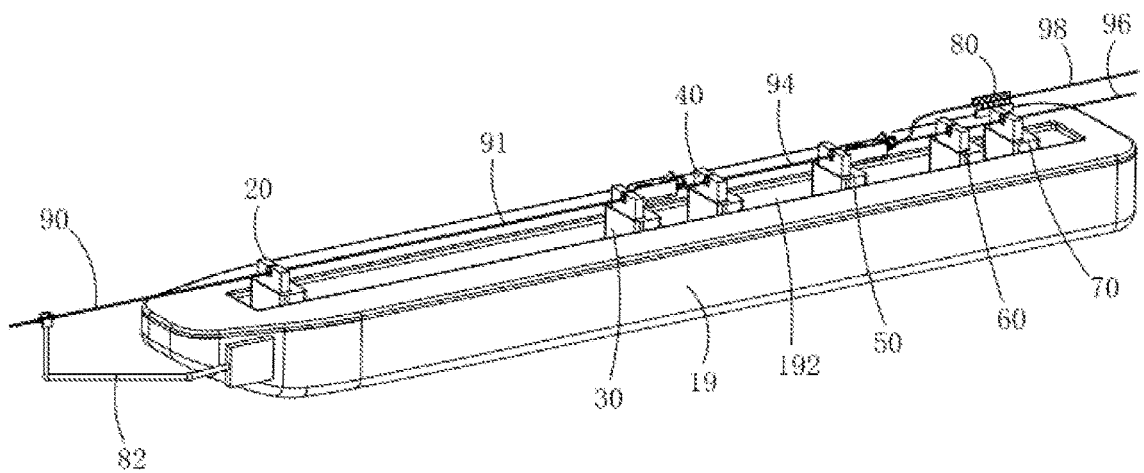
FIG. 4 is another schematic view of the slave-end apparatus in FIG. 3.

As illustrated in FIG. 3 and FIG. 4, a second embodiment of the present disclosure provides a slave-end apparatus for an interventional robot. The apparatus includes: a body 19, drive mechanisms 20, 30, 40, 50 and 60, a rear clamper 70, a rapid exchange mechanism 80 and a front clamper 82 that are movably mounted on the body 19.

The body 19 is elongated, and is provided with a linear channel 192. The drive mechanisms 20, 30, 40, 50 and 60 are successively disposed on the channel 192, and are movable along the channel. In this embodiment, the drive mechanisms 20, 30, 40, 50 and 60 may directly slide on the body 19. For example, a linear guide rail is fixed on the body 19, and the drive mechanisms 20, 30, 40, 50 and 60 may all slide along the guide rail.

Each of the drive mechanisms is configured to clamp, push (including forward movement and backward movement) and rotate (including forward rotation and reverse rotation) the catheter and the guide wire, or may be configured to simultaneously clamp, push (including forward movement and backward movement) and rotate (including forward rotation and reverse rotation) both the catheter and the guide wire, such that a plurality of catheters and one guide wire collaboratively move. Each of the drive mechanisms includes: a clamping assembly configured to clamp the catheter or the guide wire, and a rotating assembly configured to rotate the catheter or the guide wire. The rotating assembly may be an active rotating assembly or a passive rotating assembly. The rotating assemblies may be all active rotating assemblies, or may be partially active rotating assemblies and partially passive rotating assemblies. Clamping of the catheters by the drive mechanisms 20 and 40 does not hinder rotation of the catheters.

The clamping assemblies and rotating assemblies of the drive mechanisms 20, 30, 40, 50 and 60 may be the slave-end guide wire and catheter twisting apparatus for the interventional robot as disclosed in Chinese Patent Application No. 202110674959.3, the disclosure of which is incorporated herein in its entirety.

In other embodiments, the specific structures of the drive mechanisms 20, 30, 40, 50 and 60 are not necessarily identical, but may be different from each other, as long as the catheter and the guide wire can be clamped, pushed and/or rotated. Optionally, the clamping assemblies may be identical, but the rotating assemblies may be different; or the clamping assemblies may be different, but the rotating assemblies may be identical; or some of the clamping assemblies and rotating assemblies may be identical, and the others of the clamping assemblies and rotating assemblies may be different.

In this embodiment, the drive mechanisms 20 and 30 are spaced apart from each other, and are configured to cooperate with each other to clamp, push and rotate a same guide catheter 90 (that is, a first catheter) to prevent the guide catheter 90 from being bent. In fact, it is preferable that the drive mechanisms 20 and 30 synchronously push the guide catheter 90, such that the guide catheter 90 is stretched straight, without being bent. Likewise, the drive mechanisms 40 and 50 are spaced apart from each other, and are configured to cooperate with each other to clamp, push and rotate a same multifunctional catheter 91 (that is, a second catheter, or also referred to as a middle catheter). The drive mechanism 60 is configured to clamp, push and rotate a guide wire 92. The rear clamper 70 is configured to clamp and push the guide wire 92. The rapid exchange mechanism 80 and the drive mechanism 50 may be detachably fixed to each other, and may be configured to clamp and push a rapid exchange catheter.

The rear clamper 70 is positioned at a rear portion of the body 19. The front clamper 82 is positioned at a front portion of the body 19, distal to the drive mechanisms 20 and 30. In this embodiment, the front clamper 82 and the rear clamper 70 are fixed on the body 19, and may be movable relative to the body 19 where necessary. In other embodiments, the front clamper 82 and the rear clamper 70 may also be mounted separately from the body 19.

For the preparations of the operation, a guide catheter 90, a multifunctional catheter 91 and a guide wire 92 that are suitable (for example, those with suitable lengths and diameters) need to selected, and the selected guide catheter 90 and multifunctional catheter 91 are washed with normal saline and exhausted. The multifunctional catheter 91 is led into the guide catheter 90 to go beyond the guide catheter 90 by a distance, the guide wire 92 is led into the multifunctional catheter 91 to go beyond the multifunctional catheter 91 by a distance, for example, the head of the guide wire 92 goes beyond the multifunctional catheter 91 by about 10 cm. The drive mechanisms 20, 30, 40, 50 and 60 are disposed at proper positions, the guide catheter 90, the multifunctional catheter 91 and the guide wire 92 are together placed and led into an introducer (for example, femoral artery, radial artery or the like) of a patient for operation, the clamping assemblies of the drive mechanisms 20 and 30 are caused to clamp the guide catheter 90, the clamping assemblies of the drive mechanisms 40 and 50 are caused to clamp the multifunctional catheter 91, and the clamping assembly of the drive mechanism 60 and a rear clamper 70 are caused to clamp the guide wire 92. In this way, the guide catheter 90, the multifunctional catheter 91 and the guide wire 92 are fixed.

When starting the operation, a master-end console (for example, the master-end operation handle for the interventional robot as disclosed in Chinese Patent Application No. 202110654379.8 and the master-end control module as disclosed in Chinese Patent Application No. 202110649908.5, the disclosures of which are incorporated herein in their entireties) is employed to remotely manipulate the drive mechanisms 20, 30, 40, 50 and 60, the rear clamper 70 and the rapid exchange mechanism 80 to move, the master-end console is spatially isolated from a catheter room, and the master-end console and the catheter room are deployed in different regions. Specifically, the drive mechanisms 20 and 30 collaboratively clamp the guide catheter 90 and move along a channel 192 to drive the guide catheter 90 to move forward, and the rotating assemblies of the drive mechanisms 20 and 30 simultaneously or non-simultaneously rotate the guide catheter 90. In a case that the drive mechanism 20 moves to an extreme position (for example, the drive mechanism 20 moves to a distal end of the channel 192) and is to be restored to release the guide catheter 90, the drive mechanism 30 clamps the guide catheter 90 to prevent movement thereof. In a case that the drive mechanism 20 is restored to a proximal position between the front clamper and the drive mechanism 30, the clamping assembly of the drive mechanism 20 clamps the guide catheter 90 again, and the drive mechanisms 20 and 30 are caused to collaboratively drive the guide catheter 90 to move forward, and the rotating assemblies of the drive mechanisms 20 and 30 simultaneously or non-simultaneously rotate the guide catheter 90. Such operations are repeated until the guide catheter 90 moves to a desired position.

In this process, the drive mechanisms 40 and 50 simultaneously or non-simultaneously collaboratively clamp the multifunctional catheter 91 and move along the channel 192 to drive the multifunctional catheter 91 to move forward, and the rotating assemblies of the drive mechanisms 40 and 50 simultaneously or non-simultaneously rotate the multifunctional catheter 91. In a case that the drive mechanism 40 moves to an extreme position (for example, a distance from the drive mechanism 40 to the drive mechanism 30 approaches a threshold) and is to be restored to release the multifunctional catheter 91, the drive mechanism 50 clamps the multifunctional catheter 91 to prevent movement thereof. In a case that the drive mechanism 40 is restored to a proximal position between the front clamper and the drive mechanism 50, the clamping assembly of the drive mechanism 40 clamps the multifunctional catheter 91 again, the drive mechanisms 40 and 50 are caused to collaboratively drive the multifunctional catheter 91 to move forward, and the rotating assemblies of the drive mechanisms 40 and 50 simultaneously or non-simultaneously rotate the multifunctional catheter 91. Such operations are repeated until the multifunctional catheter 91 moves to a desired position.

In the above process, the drive mechanism 60 and the rear clamper 70 simultaneously or non-simultaneously collaboratively clamp the guide wire 92 and move along the channel 192 to drive the guide wire 92 to move forward, and the rotating assembly of the drive mechanism 60 simultaneously or non-simultaneously rotates the guide wire 92. In a case that the drive mechanism 60 moves to an extreme position (for example, a distance from the drive mechanism 60 to the drive mechanism 50 approaches a threshold) and is to be restored to release the guide wire 92, the rear clamper 70 clamps the guide wire 92 to prevent movement thereof. In a case that the drive mechanism 60 is restored, the clamping assembly of the drive mechanism 60 clamps the guide wire 92 again, the drive mechanism 60 and the rear clamper 70 are caused to collaboratively drive the guide catheter 92 to move forward, and the rotating assembly of the drive mechanism 60 simultaneously or non-simultaneously rotates the guide wire 92. Such operations are repeated until the guide wire 92 moves to a desired position. In other embodiments, at the beginning, only the drive mechanism 60 clamps the guide wire 92, but the rear clamper 70 does not clamp the guide wire 92. In the case that the drive mechanism 60 is restored, the rear clamper 70 clamps the guide wire 92. In a case that the drive mechanism 60 is restored and clamps the guide wire 92 again, the rear clamper 70 releases the guide wire 92. Such operations are repeated such that the drive mechanism 60 and the rear clamper 70 alternately clamp the guide wire 92.

For details about how the drive mechanisms 20, 30, 40, 50 and 60, the rear clamper 70 and the rapid exchange mechanism 80 are remotely manipulated to move by using the master-end console, reference may be made to the master-end control module for the interventional robot as disclosed in Chinese Patent Application 202110649908.5. The control module includes two operation levers, wherein one operation lever is configured to manipulate the drive mechanisms 20, 30, 40 and 50 and the rapid exchange mechanism 80, and this operation lever may manipulate the drive mechanism 20 and 30, the drive mechanisms 40 and 50 and the rapid exchange mechanism 80 in a time-division manner, and the other operation lever is configured to manipulate the drive mechanism 60 and the rear clamper 70. Optionally, the master-end console includes more than two operation levers, for example, four operation levers, which are respectively configured to remotely manipulate the drive mechanisms 20 and 30, the drive mechanisms 40 and 50, the drive mechanism 60 and the rear clamper 70, and the rapid exchange mechanism 80.

In other embodiments, the drive mechanisms 30 and 50 respectively clamp the guide catheter 90 and the multifunctional catheter 91 via an Y adapter. That is, the guide catheter 90 and the multifunctional catheter 91 are respectively connected to the Y adapter; the Y adapter is fixed to the drive mechanisms 30 and 50; and the clamping assemblies of the drive mechanisms 30 and 50 clamp the Y adapter, and the rotating assemblies of the drive mechanisms 30 and 50 rotate a Luer connector of the Y adapter to drive the guide catheter 90 and the multifunctional catheter 91 to rotate.

During collaborative pushing of the guide catheter 90, the multifunctional catheter 91 and the guide wire 92, it needs to be constantly ensured that the multifunctional catheter 91 goes beyond the guide catheter 90 by a distance and the guide wire 92 goes beyond the multifunctional catheter 91 by a distance. In a case that the guide catheter 90, the multifunctional catheter 91 and the guide wire 92 reach some positions of the vessel, the drive mechanisms 20, 30, 40, 50 and 60 and the rear clamper 70 need to be remotely manipulated by the master-end console, to drive the guide catheter 90, the multifunctional catheter 91 and the guide wire 92 to move forward and backward, and rotate forward and rotate reversely for multiple times.

In a case that the guide catheter 90 moves forward to a desired position, the guide catheter 90 is fixed. The drive mechanism 60 and the rear clamper 70 are remotely manipulated by the master-end console, to drive the guide wire 92 to move backward. The process of backward movement is similar to the above process of forward movement. In a case that the head of the guide wire 92 moves backwards to the introducer, in the catheter room, the guide wire 92 is taken off from the clamping assembly of the drive mechanism 60 and the rear clamper 70, and is soaked into the heparin water.

The guide catheter 90 is taken off from the clamping assemblies of the drive mechanisms 20 and 30, and the front clamper 82 takes over to clamp the guide catheter 90 to prevent movement thereof. It should be noted that in this process, the guide catheter 90 shall not be pushed, to prevent the head of the guide catheter 90 from moving in the vessel. The multifunctional catheter 91 is taken off from the clamping assemblies of the drive mechanisms 40 and 50, and the clamping assemblies of the drive mechanisms 20 and 30 take over to clamp the multifunctional catheter 91.

In other embodiments, the front clamper 82 may be retractable, which extends from a hidden space when a catheter needs to be clamped. With respect to the front clamper 82 configured to clamp the guide catheter 90, the front clamper 82 may also rotate the guide catheter 90 by rotating the Luer connector of the Y adapter. In other embodiments, the front portion of the body 19 is provided with a plurality of front clampers 82, and in this case, the catheter may be pushed for multiple times. In a case that each catheter is pushed to a desired position, one of the front clampers 82 is caused to clamp the catheter.

The drive mechanisms 40, 50 and 60 and the rear clamper 70 are adjusted to suitable positions. A micro catheter 94 and a micro guide wire 96 that are thinner (for example, with a diameter of 0.014 in) are selected. The micro guide wire 96 is led into the micro catheter 94 and the micro guide wire 96 and the micro catheter 94 are led into the multifunctional catheter 91, and the micro catheter 94 and the micro guide wire 96 are respectively clamped by the clamping assemblies of the drive mechanisms 40 and 50, the clamping assembly of the drive mechanism 60, and the rear clamper 70. In this way, the micro catheter 94 and the micro guide wire 96 are fixed. In other embodiments, the micro catheter 94 is connected to an Y adapter. The Y adapter is fixed to the drive mechanism 50. The clamping assembly of the drive mechanism 50 clamps the Y adapter, and the rotating assembly of the drive mechanism 50 rotates a Luer connector of the Y adapter to drive the micro catheter 94 to rotate.

Further, by using the master-end console, the drive mechanisms 20, 30, 40, 50 and 60 and the rear clamper 70 are remotely manipulated to move. For details about the specific process, reference may be made to the forward movement of the guide catheter 90, the multifunctional catheter 91 and the guide wire 92, which are thus not described herein any further. The multifunctional catheter 91 is caused to move forward to the vessel farther. In a case that the micro catheter 94 and the micro guide wire 96 move forward to the head of the multifunctional catheter 91, the micro catheter 94 and the micro guide wire 96 are further pushed to a lesion (that is, a target vessel stenosis site) of the patient for operation. The position of the micro guide wire 96 is determined by contrast radiography. In a case that the micro guide wire 96 reaches a designated position (generally, the micro guide wire 96 needs to run through the lesion of the patient for operation, except possible treatment of aneurysm embolization), the drive mechanisms 20 and 30, the drive mechanisms 40 and 50, the drive mechanism 60 and the rear clamper 70 respectively fix the multifunctional catheter 91, the micro catheter 94 and the micro guide wire 96. In a case that the micro guide wire 96 fails to reach the designated position, the drive mechanisms 20, 30, 40, 50 and 60 and the rear clamper 70 are repeatedly remotely manipulated to move, until the micro guide wire 96 reaches the designated position.

In other embodiments, the drive mechanisms 40, 50 and 60 and the rear clamper 70 may be remotely manipulated, by using the master-end console, to drive the multifunctional catheter 91 and the guide wire 92 to move backward together. In a case that the heads of the multifunctional catheter 91 and the guide wire 92 move backward to the introducer, in the catheter room, the multifunctional catheter 91 and the guide wire 92 are taken off from the clamping assemblies of the drive mechanisms 40, 50 and 60 and the rear clamper 70, and are soaked into the heparin water. Then, the guide catheter 90 is taken off from the clamping assemblies of the drive mechanisms 20 and 30, and the front clamper 82 takes over to clamp the guide catheter 90 to prevent movement thereof. It should be noted that in this process, the guide catheter 90 shall not be pushed, to prevent the head of the guide catheter 90 from moving in the vessel. Two catheters and one guide wire that are suitable are selected, and the catheters and the guide wire are placed into the guide catheter 90 all together. The drive mechanisms 20, 30, 40, 50 and 60 are caused to be at suitable positions, the clamping assemblies of the drive mechanisms 20 and 30 are caused to clamp one catheter, the clamping assemblies of the drive mechanisms 40 and 50 clamp the other catheter, and the clamping assembly of the drive mechanism 60 and the rear clamper 70 are caused to clamp the guide wire. In this way, the two catheters and the one guide wire are fixed. For details about the subsequent process of forward movement, reference may be made to the forward movement of the guide catheter 90, the multifunctional catheter 91 and the guide wire 92, which are thus not described herein any further.

In the case that the micro guide wire 96 reaches the designated position, by using the master-end console, the drive mechanisms 40 and 50 are remotely manipulated to cause the micro catheter 94 to move backward. In the meantime, the micro guide wire 96 is maintained as not moving. For example, as the drive mechanism 60 moves backward, the rear clamper 70 takes over to clamp the micro guide wire 96 to prevent movement thereof. In a case that the head of the micro catheter 94 moves backward to the introducer, in the catheter room, the micro catheter 94 is taken off from the drive mechanisms 40 and 50, and is soaked into the heparin water. In this case, the drive mechanism 60 may take over to clamp the micro guide wire 96, and maintain the front clamper 82, the drive mechanisms 20 and 30 and the drive mechanism 60 as respectively fixing the guide catheter 90, the multifunctional catheter 91 and the micro guide wire 96.

Further, in the catheter room again, the tail of the micro guide wire 96 is caused to run into a rapid exchange balloon dilatation catheter 98. The rapid exchange balloon dilatation catheter 98 moves forward along with the micro guide wire 96. In this case, the rapid exchange mechanism 80 clamps the rapid exchange balloon dilatation catheter 98.

Further, by using the master-end console, the rapid exchange mechanism 80 is remotely manipulated, such that the rapid exchange balloon dilatation catheter 98 moves forward to the lesion of the patient for operation (not going beyond the head of the micro guide wire 96). In this process, the position and angle of the micro guide wire 96 need to be finely adjusted by forward rotation, reverse rotation, forward movement, and backward movement according to actual needs. In a case that the rapid exchange balloon dilatation catheter 98 reaches the lesion of the patient for operation, a contrast medium is filled into the rapid exchange balloon dilatation catheter 98 in the catheter room for pre-dilatation, and a vasodilation effect is determined by contrast radiography. In a case that the vasodilation effect is achieved, the contrast medium is extracted from the rapid exchange balloon dilatation catheter 98. Further, by using the master-end console, the rapid exchange mechanism 80 is remotely manipulated to move backward to the introducer. In the process that the rapid exchange balloon dilatation catheter 98 moves backwards, the position of the micro guide wire 96 remains unchanged. With respect to some operations, vasodilation needs to be performed for multiple times. Therefore, the rapid exchange balloon dilatation catheter may move forward and move backward for multiple times.

Further, in the catheter room again, the rapid exchange balloon dilatation catheter 98 is taken off from the rapid exchange mechanism 80, and then a balloon-expandable stent catheter is caused to run into the micro guide wire 96 and to be clamped on the rapid exchange mechanism 80. For details about the specific process, reference may be made to the above process of the rapid exchange balloon dilatation catheter 98, which are thus not described herein any further.

Further, by using the master-end console, the rapid exchange mechanism 80 is remotely manipulated, such that the rapid exchange balloon dilatation catheter is pushed along the micro guide wire 96 to the lesion of the patient for operation (a narrow vessel site that has been expanded). In this process, the position and angle of the micro guide wire 96 are finely adjusted by forward rotation, reverse rotation, forward movement, and backward movement according to actual needs. When the rapid exchange balloon-expandable stent catheter reaches the lesion of the patient for operation (the vessel side that has been expanded), the position of the rapid exchange balloon-expandable stent catheter is fine-tuned, after determination, the rapid exchange balloon-expandable stent catheter is filled with the contrast medium in the catheter room, such that the stent is shaped. It is confirmed by contrast radiography that the placement of the balloon expandable stent is correct, i.e., the contrast medium may be extracted and the rapid exchange mechanism 80 is manipulated to drive the rapid exchange balloon-expandable stent catheter to move backward to the introducer, whereas the balloon-expandable stent remains in the lesion of the patient for operation. In the catheter room, the rapid exchange balloon-expandable stent catheter is taken from the rapid exchange mechanism 80, and is put into the heparin water.

Further, by using the master-end console, the drive mechanisms 20, 30, 40, 50 and 60 and the rear clamper 70 are remotely manipulated to move, such that the multifunctional catheter 91 and the micro guide wire 96 move backward to the introducer. Finally, in the catheter room, the multifunctional catheter 91 and the micro guide wire 96 are taken off from the clamping assemblies of the drive mechanisms 20, 30 and 60 and the rear clamper 70, the guide catheter 90 is taken from the front clamper 82, the multifunctional catheter 91, the micro guide wire 96 and the guide catheter 90 are withdrawn from the introducer and placed into the heparin water, and then the introducer is removed and post-operation treatment is carried out to complete the operation.

In the above process, the rapid exchange catheter is used, and therefore, the catheter needs to be clamped, pushed and rotated by a rapid exchange mechanism 80. In a case that a coaxial exchange catheter is used, where the tail of the micro guide wire 96 is caused to run into the coaxial exchange catheter, the coaxial exchange catheter is clamped, pushed and rotated by the coaxial exchange mechanism, such that the coaxial exchange catheter moves forward to an appropriate position along the micro guide wire 96 or moves backward to the introducer. Regardless of the rapid exchange mechanism 80 or the coaxial exchange mechanism, the clamping, pushing and rotating of the rapid exchange catheter and the coaxial exchange catheter may be practiced by means of roller driving.

Figure 5:
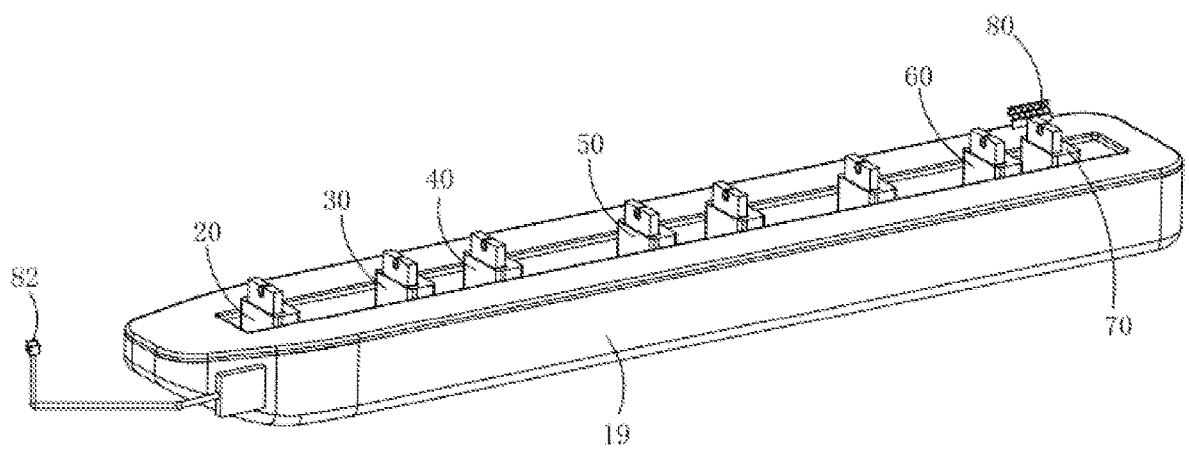
FIG. 5 is a schematic view of the slave-end apparatus in FIG. 3 in which two drive mechanisms are added.
Figure 6:
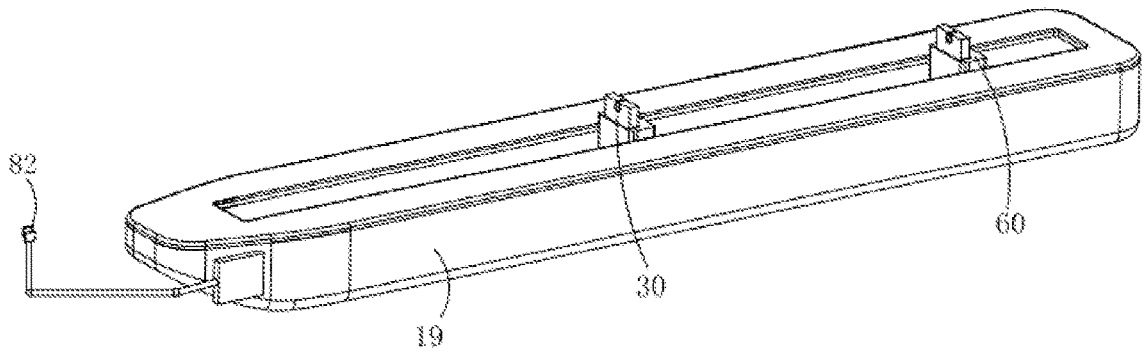
FIG. 6 is a schematic view of the slave-end apparatus in FIG. 3 in which only two drive mechanisms are remained.

In the above, the movement and control process of the present disclosure has been described by taking "balloon-expandable stent angioplasty" as an example. Indeed, the present disclosure may also be used in a variety of procedures including contrast radiography, embolization, thrombectomy, and the like. The drive mechanisms 20, 30, 40, 50 and 60, the rear clamper 70 and the rapid exchange mechanism 80 may be freely adapted according to the actual needs of the operation, i.e., the drive mechanisms 20, 30, 40, 50 and 60, the rear clamper 70 and the rapid exchange mechanism 80 may all be easily disassembled and assembled. Where more complicated surgeries are performed, more drive mechanisms, rear clampers and rapid exchange mechanisms may be deployed. In a case that more drive mechanisms and rear clampers are deployed, the collaborative movement of a plurality of catheters corresponding to one guide wire or corresponding to a plurality of guide wires may be practiced. As illustrated in FIG. 5, two drive mechanisms are added to clamp and rotate more catheters. For details, reference may be made to the above-mentioned "balloon stent angioplasty." A rapid exchange mechanism is provided for each drive mechanism that constantly clamps the catheter, and is either removably mounted to the drive mechanism or integrally formed with the drive mechanism. In case of performing simple examination procedures, such as an angiographic procedure, only two of the drive mechanisms 20, 30, 40, 50 and 60, such as the drive mechanisms 30 and 60, are used. Referring to FIG. 6, the other drive mechanisms, the rear clamper 70 and the rapid exchange mechanism 80 are removed from the body 19.

In the above description, the master-end console and the operable table on which the master-end console is deployed are outside the catheter room. In fact, the master-end console and the operable table may also be deployed in a separate space in the catheter room, as long as X-ray radiation can be isolated and the physician is exempt from the X-ray radiation.

The above only describes how the catheter and the guide wire are replaced in some cases. In fact, the replacement of the catheter and the guide wire may be completely determined according to the actual needs of the operation and the personal operating habits. The placement is not limited to the above methods for replacing the catheter and the guide wire.

According to the present disclosure, the first drive mechanism and the second drive mechanism may be remotely manipulated to move along the same axial direction on the body, such that a plurality of catheters and a plurality of guide wires collaboratively move to desired positions. In case of replacing the catheter and the guide wire, the front clamper clamps the first catheter to prevent movement thereof. This blocks radiation by X rays and protects health of human bodies. In addition, the robot may more accurately control the catheter and the guide wire, which not only reduces working intensity, but also avoids severe mistakes.

Persons of ordinary skill in the art should understand that all or part of steps of the method may be implemented by programs instructing related hardware. The programs may be stored in a computer-readable storage medium, for example, a read-only memory, a magnetic disk, or a compact disc read-only memory. Alternatively, all or part of the steps of the embodiments described above may be implemented using one or more integrated circuits. Accordingly, various modules/units in the above-mentioned embodiments may be implemented in the form of hardware or in the form of software functional modules. The present disclosure is not limited to any specific form of hardware or software combination.

Nevertheless, many other embodiments may also be available for implementation of the present disclosure, and those skilled in the art would recognize that various modifications and changes may be made thereto without departing from the spirit and scope of the present disclosure. These modifications and changes fall within the protection scope set forth in the appended claims.

Described are merely exemplary embodiments of the present disclosure, but are not intended to limit the present disclosure. Any modification, equivalent replacement, and improvement made without departing from the spirit and principle of the present disclosure shall fall within the protection scope of the present disclosure.

What is claimed is:

1. A slave-end apparatus for an interventional robot, comprising: a body, and a first drive mechanism, a second drive mechanism, a third drive mechanism and a front clamper distal to the first drive mechanism that are successively mounted on the body; wherein the front clamper is positioned at a front side of the body and configured to be retractable between an extended position where the front clamper moves to an outside of the body along an extending direction of the body and a hidden position where the front clamper moves back onto the body relative to the front of the body, the first drive mechanism is configured to clamp and rotate a first catheter and a second catheter, the second drive mechanism is configured to clamp and rotate the second catheter and a third catheter, and the third drive mechanism is configured to clamp and rotate a first guide wire and a second guide wire; and in a case that the first guide wire runs into the second catheter, the second catheter runs into the first catheter, and the first guide wire, the second catheter and the first catheter are respectively clamped by the third drive mechanism, the second drive mechanism and the first drive mechanism and move along a same axial direction on the body toward the front clamper to a desired position, the first catheter, the second catheter and the first guide wire are respectively taken off from the first drive mechanism, the second drive mechanism and the third drive mechanism, the front clamper and the first drive mechanism take over to clamp the first catheter and the second catheter, the third catheter is caused to run into the second catheter and the second guide wire is caused to run into the third catheter, and the third catheter and the second guide wire are respectively clamped by the second drive mechanism and the third drive mechanism and move along the same axial direction on the body toward the front clamper;

wherein the first drive mechanism and the second drive mechanism are configured to collaboratively clamp the first guide catheter to drive the first guide catheter to move forward, when the first drive mechanism moves to an extreme position and is to be restored to release the first guide catheter, the second drive mechanism is configured to clamp the first guide catheter to prevent movement thereof; when the first drive mechanism is restored to a proximal position between the front clamper and the second drive mechanism, the first drive mechanism is configured to clamp the first guide catheter again, and the first drive mechanism and the second drive mechanism are configured to collaboratively drive the first guide catheter to move forward again, in such way that operations are repeated until the first guide catheter moves to a desired position;

wherein the front clamper is configured to be connected with an Y adapter connected to the first catheter and to rotate a Luer connector of the Y adapter to drive the first catheter to rotate.

2. The slave-end apparatus for the interventional robot according to claim 1, further comprising: a plurality of front clampers; wherein a plurality of first catheters one-by-one pushed by the first drive mechanism to desired positions are respectively clamped by the plurality of front clampers.

3. The slave-end apparatus for the interventional robot according to claim 1, wherein the second drive mechanism is configured to clamp and rotate, together with the first drive mechanism, the first catheter and the second catheter; the second drive mechanism comprises: a first assembly configured to clamp and rotate the first catheter and the second catheter, and a second assembly configured to clamp and rotate the second catheter and the third catheter.

4. The slave-end apparatus for the interventional robot according to claim 3, wherein the first drive mechanism and the second mechanism are configured to collaboratively clamp the first guide catheter to drive the first guide catheter to move forward, when the first drive mechanism moves to an extreme position and is to be restored to release the first guide catheter, the second drive mechanism is configured to clamp the first guide catheter to prevent movement thereof; when the first drive mechanism is restored to a position proximal to the second drive mechanism, the first drive mechanism is configured to clamp the first guide catheter again, and the first drive mechanism and the second mechanism are configured to collaboratively drive the first guide catheter to move forward again, in such way operations are repeated until the first guide catheter moves to a desired position.

5. The slave-end apparatus for the interventional robot according to claim 4, wherein the first assembly of the second drive mechanism is configured to clamp an Y adapter connected to the first catheter and the second catheter to clamp the first catheter and the second catheter, and rotate a Luer connector of the Y adapter to drive the first catheter and the second catheter to rotate.

6. The slave-end apparatus for the interventional robot according to claim 3, wherein the third drive mechanism is configured to clamp and rotate, together with the second drive mechanism, the second catheter and the third catheter; the third drive mechanism comprises: a first assembly configured to clamp and rotate the second catheter and the third catheter, and a second assembly configured to clamp and rotate the first guide wire and the second guide wire.

7. The slave-end apparatus for the interventional robot according to claim 6, the front clamper is configured to be connected with an Y adapter connected to the first catheter and to rotate a Luer connector of the Y adapter to drive the first catheter to rotate.

8. The slave-end apparatus for the interventional robot according to claim 6, wherein the first assembly of the third drive mechanism is configured to clamp an Y adapter connected to the second catheter and the third catheter to clamp the second catheter and the third catheter, and rotate a Luer connector of the Y adapter to drive the second catheter and the third catheter to rotate.

9. The slave-end apparatus for the interventional robot according to claim 1, further comprising: a fourth drive mechanism mounted on the body; wherein the fourth drive mechanism is configured to clamp and rotate, together with the first drive mechanism, the first catheter and the second catheter.

10. The slave-end apparatus for the interventional robot according to claim 9, wherein in a case that the first drive mechanism moves to an extreme position and is to be restored to release the first catheter and the second catheter, the fourth drive mechanism is configured to clamp the first catheter and the second catheter to prevent movement thereof.

11. The slave-end apparatus for the interventional robot according to claim 9, wherein the fourth drive mechanism is positioned between the first drive mechanism and the second drive mechanism.

12. The slave-end apparatus for the interventional robot according to claim 9, further comprising: a fifth drive mechanism mounted on the body; wherein the fifth drive mechanism is configured to clamp and rotate, together with the second drive mechanism, the second catheter and the third catheter.

13. The slave-end apparatus for the interventional robot according to claim 12, wherein in a case that the second drive mechanism moves to an extreme position and is to be restored to release the second catheter and the third catheter, the fifth drive mechanism is configured to clamp the second catheter and the third catheter to prevent movement thereof.

14. The slave-end apparatus for the interventional robot according to claim 12, wherein the fifth drive mechanism is positioned between the second drive mechanism and the third drive mechanism.

15. The slave-end apparatus for the interventional robot according to claim 12, wherein the fourth drive mechanism and the fifth drive mechanism move along the same axial direction as the first drive mechanism, the second drive mechanism and the third drive mechanism.

16. The slave-end apparatus for the interventional robot according to claim 1, further comprising: an exchange mechanism; wherein the exchange mechanism is a rapid exchange mechanism or a coaxial exchange mechanism.

17. The slave-end apparatus for the interventional robot according to claim 16, wherein the exchange mechanism is detachably fixed to the third drive mechanism, or the exchange mechanism and the third drive mechanism are integrally designed.

* * * * *